(12) United States Patent
Prass

(10) Patent No.: US 8,452,370 B2
(45) Date of Patent: May 28, 2013

(54) SINGLE AND MULTI-NEEDLE ELECTROMYOGRAPHIC (EMG) RECORDING ELECTRODE CONFIGURATIONS FOR INTRAOPERATIVE NERVE INTEGRITY MONITORING

(75) Inventor: Richard L. Prass, Nashville, TN (US)

(73) Assignee: Richard L. Prass, Nashville, TN (US)

( * ) Notice: Subject to any disclaimer, the term of this patent is extended or adjusted under 35 U.S.C. 154(b) by 430 days.

(21) Appl. No.: 12/686,893

(22) Filed: Jan. 13, 2010

(65) Prior Publication Data

US 2010/0179410 A1    Jul. 15, 2010

Related U.S. Application Data

(60) Provisional application No. 61/144,195, filed on Jan. 13, 2009, provisional application No. 61/144,196, filed on Jan. 13, 2009, provisional application No. 61/144,198, filed on Jan. 13, 2009, provisional application No. 61/144,201, filed on Jan. 13, 2009, provisional application No. 61/144,202, filed on Jan. 13, 2009, provisional application No. 61/144,205, filed on Jan. 13, 2009, provisional application No. 61/144,209, filed on Jan. 13, 2009.

(51) Int. Cl.
*A61B 5/0492* (2006.01)

(52) U.S. Cl.
USPC .............. 600/373; 600/546; 600/547

(58) Field of Classification Search
USPC .......................................... 600/373, 546, 547
See application file for complete search history.

(56) References Cited

U.S. PATENT DOCUMENTS

| | | | |
|---|---|---|---|
| 5,161,533 A | | 11/1992 | Prass et al. |
| 5,482,038 A | * | 1/1996 | Ruff .............................. 600/372 |
| 5,593,429 A | * | 1/1997 | Ruff .............................. 607/116 |
| 6,306,100 B1 | * | 10/2001 | Prass ............................. 600/554 |
| 7,310,546 B2 | * | 12/2007 | Prass ............................. 600/373 |

* cited by examiner

*Primary Examiner* — Lee S Cohen
(74) *Attorney, Agent, or Firm* — Ronald E. Prass, Jr.; Prass LLP

(57) ABSTRACT

Several configurations for single and multi-needle electromyographic (EMG) recording electrodes for intraoperative nerve integrity monitoring are disclosed, one of which may concern a multi-needle electrode including one or more cables that are connected directly or indirectly to a nerve integrity monitor, a single hub connected to the one or more cables, and at least two needle electrodes connected to the single hub each having first and second bends along the line of insertion into a patient, wherein the first bend occurs at the hub connection in a downward direction and the second bend occurs in an upward direction from the first bend creating a proximal needle segment from the hub to the second bend and a terminal needle segment from the second bend to the end of each needle.

24 Claims, 11 Drawing Sheets

SINGLE AND MULTI-NEEDLE ELECTROMYOGRAPHIC (EMG) RECORDING ELECTRODE CONFIGURATIONS FOR INTRAOPERATIVE NERVE INTEGRITY MONITORING

PRIORITY APPLICATION INFORMATION

This application claims priority from U.S. Provisional Patent Application Ser. No. 61/144,195, filed Jan. 13, 2009, U.S. Provisional Patent Application Ser. No. 61/144,196, filed Jan. 13, 2009, U.S. Provisional Patent Application Ser. No. 61/144,198, filed Jan. 13, 2009, U.S. Provisional Patent Application Ser. No. 61/144,201, filed Jan. 13, 2009, U.S. Provisional Patent Application Ser. No. 61/144,202, filed Jan. 13, 2009, U.S. Provisional Patent Application Ser. No. 61/144,205, filed Jan. 13, 2009, and U.S. Provisional Patent Application Ser. No. 61/144,209, filed Jan. 13, 2009, the contents of which are incorporated herein by reference in their entireties.

BACKGROUND OF THE DISCLOSED EMBODIMENTS

1. Field of the Disclosed Embodiments

The disclosed embodiments may relate to medical equipment and in particular, to a configurations of single and multi-needle electromyographic (EMG) recording electrodes for nerve integrity monitoring.

2. Introduction

Intraoperative nerve integrity monitoring involves sonic and graphic display of EMG activity from target muscles of nerves at risk for surgical injury. The technique may be applied to any motor nerve at risk for surgical injury, providing that its target muscles are accessible for EMG recording. Sonic feedback, elicited by electrical stimulation or mechanical manipulations of the monitored nerve, allows the surgeon to be more aware of the location and physical contour of the monitored nerve(s), as well as, the possible injurious effects of surgical manipulations.

Largely due to the general effectiveness of nerve integrity monitoring, its use during surgical procedures has significantly expanded. This expansion has increased the number of new and inexperienced end users. In addition, changes in reimbursement for monitoring procedures have caused a shift from physician to allied medical personnel-based equipment setup. The inexperience of end users and the lack of standardized initial recording and stimulus setup procedures for nerve integrity monitoring may lead to severe medical consequences for patients.

SUMMARY OF THE DISCLOSED EMBODIMENTS

A several configurations for single and multi-needle electromyographic (EMG) recording electrodes for intraoperative nerve integrity monitoring are disclosed. One possible embodiment may concern a modification of single or multi-needle electrodes with a single hub. The proposed modification may incorporate two bends in the needle portion of the electrodes along the line of needle insertion. The first bend may occur at the hub in a purely downward direction. The magnitude of the first bend may be 90 degrees or more. The second bend is in the opposite direction of the first bend, the angle of which may vary, depending upon the intended orientation and depth of the terminal needle segment. In order for proper insertion, the depth of initial insertion of the terminal needle segment may be equal to the length of the portion of the proximal needle segment below the lower border of the hub. The full length of the terminal segment may be equal to or longer than the depth of initial insertion.

The disclosed embodiments may also concern a modification for single and multi-needle EMG electrodes with an offset configuration. The modification may include a concave groove and a relatively prominent upper ridge along the sides of the hub. The ridge and groove along the upper side-edges of the hub may improve the ability to manually manipulate the hub when it is parallel with, and close to, the skin. The ridge and groove may be particularly helpful in maintaining a slight elevation of the electrode tip, in order to maintain the hub in a plane parallel to the skin surface, as the electrode is advanced forward to its final position. The ridge along the upper edge of the sides of the electrode hub may be a possible alternative to increasing the hub thickness in order to achieve better tactile feedback and manipulative control during placement.

The disclosed embodiments may further concern a modification of the ground electrode, where the electrode hub is physically, but not necessarily electrically, attached to the lead wires of the recording electrode(s). The attachment may be fixed, detachable or adjustable in position along the length of the lead wires, depending upon the requirements of individual applications. With such an attachment, the recording electrode lead wires may be supported and organized around a strategic placement position for the ground electrode.

The disclosed embodiments may further concern a modification of a modified ground electrode, where the electrode leads may be attached to the hub of the ground electrode. In this case, however, there may be hard electrical connections within the hub of the ground electrode, connecting the terminal and proximal portions of the recording electrode leads. In this manner, the delicate and stable attributes of hooked-wire electrodes and the robustness of standard electrode leads may be combined. The inserted portion of the electrode may be a bipolar fine hooked-wire electrode, the lead length of which may be limited to only that required for unencumbered insertion into the target muscle tissue and subsequent placement of the hub at a particular location.

The disclosed embodiments may further concern a modification of needle electrodes with "offset" configuration, specifically with regard to the positioning of the electrode needles on the hub. The "offset" needle electrodes may be constructed so that the front edge of the hub can serve as a guide to the proper insertion depth for individual applications. Placement of the needle on the hub may vary for different depths of insertion, depending upon the specific application. For example, intramuscular placement may require a greater insertion depth than subdermal placement.

The disclosed embodiments may further concern a modification of a paired electrode design where a third needle electrode may be located symmetrically between the paired recording electrodes and serves as the ground electrode. The needle electrodes may be straight or modified with an offset configuration. The electrode leads may be taped together at intervals, twisted together or braided in order to minimize the antenna-like qualities of the electrode leads themselves.

The disclosed embodiments may further concern the elimination for the need for a separate stimulus anode electrode during monopolar electrical stimulation and reduces possible localization ambiguity during bipolar stimulation. A separate anode electrode connection to the patient may be eliminated by connection of the ground electrode to the anode in the stimulus circuit. This can be accomplished before or after the electrical isolation circuitry, but not across it. For example, an exemplary electrical connection between the ground electrode and the anode terminal before the isolation circuit, which may be enclosed inside the electrode connection ("head") box. An alternative embodiment may involve making the connection between the ground and anode "after" the electrical isolation circuit and within the main unit.

BRIEF DESCRIPTION OF THE DRAWINGS

In order to describe the manner in which the above-recited and other advantages and features of the disclosed embodiments can be obtained, a more particular description of the disclosed embodiments briefly described above will be rendered by reference to specific embodiments thereof which are illustrated in the appended drawings. Understanding that these drawings depict only typical disclosed embodiments and are not therefore to be considered to be limiting of its scope, the disclosed embodiments will be described and explained with additional specificity and detail through the use of the accompanying drawings in which.

DETAILED DESCRIPTION OF THE DISCLOSED EMBODIMENTS

Figure 1A:
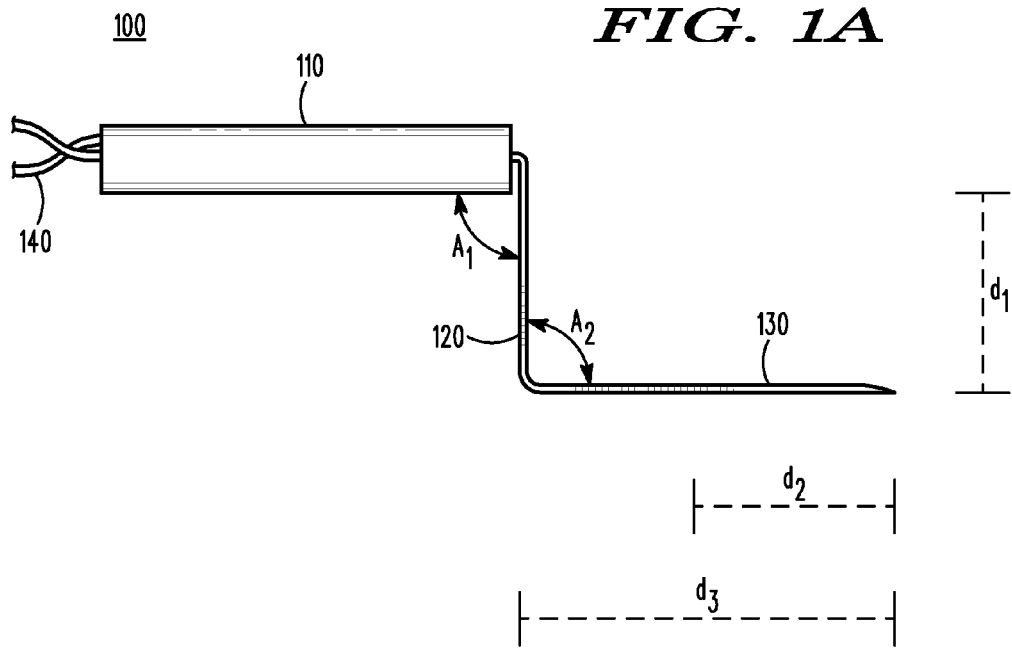
FIG. 1A is a side view of needle modification of single or multi-needle electrodes with 90 degree angles at A1 and A2 in accordance with one possible embodiment of the disclosure.

Additional features and advantages of the disclosed embodiments will be set forth in the description which follows, and in part will be obvious from the description, or may be learned by practice of the disclosed embodiments. The features and advantages of the disclosed embodiments may be realized and obtained by means of the instruments and combinations particularly pointed out in the appended claims. These and other features of the disclosed embodiments will become more fully apparent from the following description and appended claims, or may be learned by the practice of the disclosed embodiments as set forth herein.

The disclosed embodiments are discussed in detail below. While specific implementations are discussed, it should be understood that this is done for illustration purposes only. A person skilled in the relevant art will recognize that other components and configurations may be used without parting from the spirit and scope of the disclosed embodiments.

The disclosed embodiments may relate to a modification of single and multi-needle electromyographic (EMG) recording electrodes, intended to improve reliability and stability of intramuscular placement during intraoperative nerve integrity monitoring. An aim of this technology is to achieve design-driven improvements in standardization and ease of performing setup procedures, regardless of experience and training among end users and support personnel. The disclosed embodiments are intended to facilitate and standardize the initial recording and stimulus setup procedures for nerve integrity monitoring. The disclosed embodiments are set forth as follows:

1. Modification of Needle EMG Electrodes for Intraoperative Nerve Integrity Monitoring The disclosed embodiments may relate to a modification of single and multi-needle electromyographic (EMG) recording electrodes, intended to improve reliability and stability of intramuscular placement during intraoperative nerve integrity monitoring. Intraoperative nerve integrity monitoring may involve sonic and graphic display of EMG activity from target muscles of nerves at risk for surgical injury. The technique may be applied to any motor nerve at risk for surgical injury, providing that its target muscles are accessible for EMG recording. Sonic feedback, elicited by electrical stimulation or mechanical manipulations of the monitored nerve, may allow the surgeon to be more aware of the location and physical contour of the monitored nerve(s), as well as, the possible injurious effects of surgical manipulations.

The most effective method of recording EMG activity for nerve integrity monitoring may be achieved with intramuscular electrode placement. Intramuscular recording may afford sensitive detection of large, small, time-concerted and time-dispersed EMG signals with a relatively narrow dynamic range. Such dynamic range compression characteristics may be ideal for sensitive detection of a wide variety of mechanically and electrically stimulated responses at a single equipment setting. Intramuscularly recorded EMG signals may typically be polyphasic and relatively readily distinguishable from most electrical artifacts.

Intraoperative nerve integrity monitoring is most commonly used for facial nerve monitoring during ear, parotid and skull base surgery. Because facial muscles are located close to the skin surface, intramuscular placement may be achieved with relatively short needle electrodes. Standard 1 cm subdermal needle electrodes have been commonly used successfully for this purpose.

A limitation of uninsulated needle electrodes is that a significant proportion of the needle electrode may be in contact with inactive tissue, such as skin and underlying subcutaneous fat and connective tissue. Due to a typically shallow, 20-30 degrees, angle of needle insertion, the length of contact with inactive tissue may be 2-3 times the 1.5 mm skin thickness itself. Thus, nearly 25-30% of 10-12 mm subdermal electrodes may be in contact with electrically inactive skin tissue. The thickness of underlying subcutaneous tissue and fat is more variable, but may be an additional 2-4 mm.

Depending upon the thickness of underlying subcutaneous tissue and fat, a minority of the electrode length may actually be in contact within electrically active intramuscular tissue. Contact of recording electrodes with inactive tissue degrades recording quality for nerve integrity monitoring by dampening/reducing the amplitude of recorded EMG signals. A polytetrafluoroethylene coating such as a TEFLON coating of the proximal portion of the electrode needles has been used in a paired-needle electrode design (U.S. Pat. No. 5,161,533), in order to reduce or eliminate electrode contact with inactive skin and subcutaneous tissue.

Straight needle electrodes are most securely held with the index finger under, and the thumb positioned over the top of the electrode hub. However, the index finger under the hub makes is awkward to achieve an acute 20-30 degree insertion angle. Longer needle length has been employed in order to facilitate a secure grip of straight needle electrodes for placement at a shallow angle (see e.g., U.S. Pat. No. 5,161,533, the contents of which are incorporated by reference in its entirety). However, sales patterns suggest that consumers prefer the shorter electrode lengths.

Once placed, straight needle electrodes are typically secured by placing adhesive tape over the hub. Depending upon the angle of placement, the needle hub may stick up to a greater or lesser degree. The angle is usually greater with shorter needles. Taping over a needle hub that is sticking up may locally distort tissues in the recording area, possibly causing the needle to cut through small blood vessels, especially in the orbicularis oculi muscle area. The lack of a flat relationship with the skin surface may also destabilize the placement, rendering the electrode more likely to slide under the adhesive tape. In practice, a small coil of lead-wire is often taped to the skin, close to the electrode placement site, in order to provide "strain relief" as a preventative measure against dislodgement with inadvertent electrode lead manipulations.

The disclosed embodiments may concern a modification of needle EMG electrodes that may be intended to improve the ease, as well as, the reliability and stability of intramuscular placement. The needle electrodes of the disclosed embodiments may effectively appear shorter to the end user, which may aid in user comfort and acceptance.

Figure 1B:
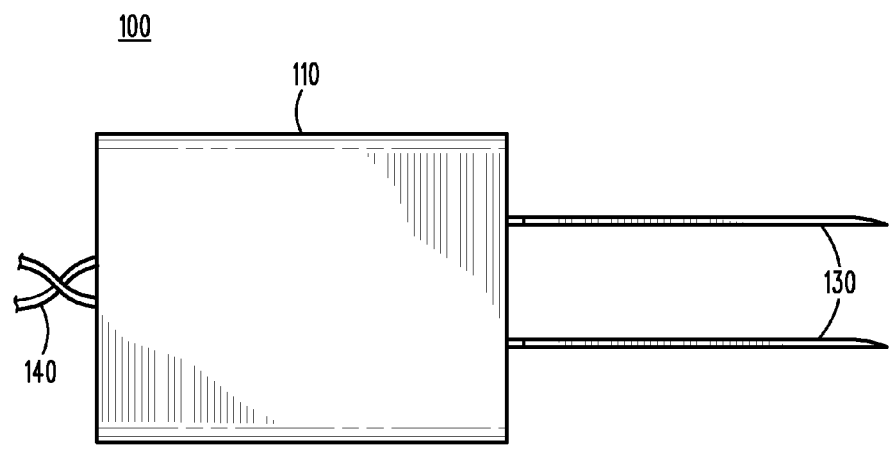
FIG. 1B is a top view of needle modification of single or multi-needle electrodes with 90 degree angles at A1 and A2 in accordance with one possible embodiment of the disclosure.

In particular, the disclosed embodiments may concern a modification of single or multi-needle electrodes with a single hub 110. The single hub may be connected using one or more cables 140 directly or indirectly to a nerve integrity monitor (not shown) (NOTE: for the purposes of further discussions concerning the remaining embodiments, it will be assumed that any hub that is shown in any of the figures may be connected using one or more cables directly or indirectly to a nerve integrity monitor). Conventional EMG needle electrodes for intraoperative nerve integrity monitoring are straight. The modification in the disclosed embodiments may incorporate one or more electrodes that each comprise a proximal needle segment 120 and a terminal needle segment 130 and each having two bends in the needle portion of the electrodes along the line of needle insertion, as shown in FIGS. 1A and 1B, for example. The first bend A1 may occur at the hub 110 in a downward direction and may create the proximal needle segment 120. The magnitude of A1 may be substantially 90 degrees from the hub (the hub being positioned horizontally as in the figure) or may be at some other lesser angle, for example. The second bend A2 is in the opposite direction of A1 which may create the terminal needle segment 130, the angle of which may vary, depending upon the intended orientation and depth of the terminal needle segment 130.

In order for proper insertion, the depth of initial insertion d2 of the terminal needle segment 130 should be equal to the length of the portion of the proximal needle segment 120 below the lower border d1 of the hub 110. The full length d3 of the terminal segment 130 may be equal to or longer than d2.

Figure 2:
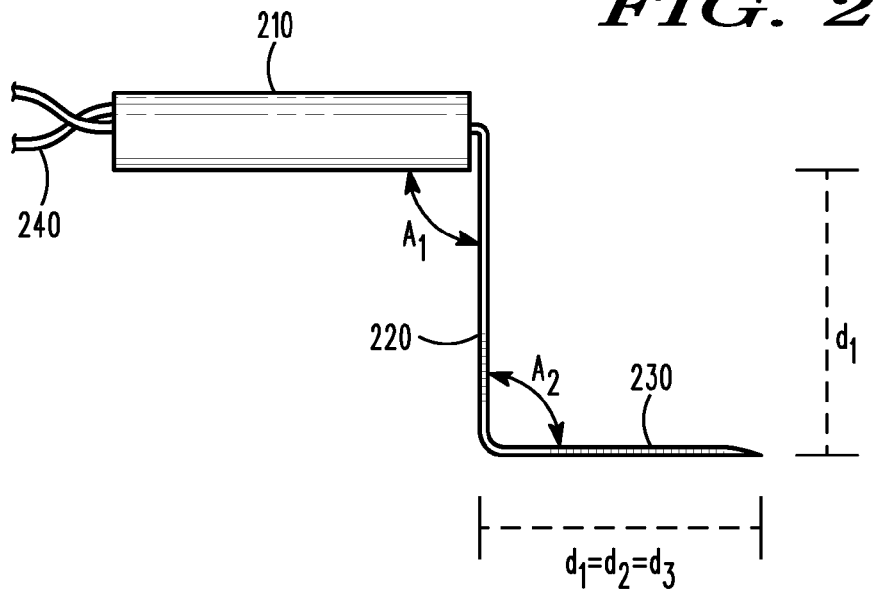
FIG. 2 is a "special" embodiment of needle modification of single or multi-needle electrodes with 90 degree angles at A1 and A2 in accordance with one possible embodiment of the disclosure.

A "special" embodiment incorporates equal lengths of d1, d2, and d3. With equal lengths of proximal needle segment 120 and terminal needle segment 130 the entire terminal segment 130 may be inserted into the skin. FIG. 2 shows such an embodiment with both A1 and A2 at substantially 90 degree angles. The terminal segment 230 of the needle electrode may be inserted at an angle with the skin surface equal to the angle at A1 (e.g., substantially 90 degrees). The terminal needle segment(s) 230 may be completely inserted to the level of A2, with the bend at A2 serving as a depth guide. The hub 210 may then be rotated backward so that its undersurface is roughly parallel with the skin surface. Final positioning of the electrode may be achieved by advancing the hub 210 forward, while maintaining the "parallel with the skin" orientation of the hub 210. This may be best achieved with the index finger and thumb on opposite sides of the hub 210. Pressure may be applied to the sides of the hub 210 so as to tip the electrode slightly upward as the hub 210 is advanced forward. During forward advancement of the hub 210, the applied force should be exclusively parallel with the skin surface. When the hub 210 has been advanced adequately, the electrode may drop into place, as the proximal needle segment 220 enters the initial needle tract.

There are several potential advantages of this electrode needle modification. When the electrode is properly inserted, the hub 210 may lie flat on, and parallel to, the skin surface. The "flat, parallel to the skin" post-placement positioning may provide a quality assurance guide for proper electrode placement and, thus, may increase consistency and reliability of placement. When the electrode is properly placed, the intended depth and orientation of the needle terminus may be assured.

This modification may be relatively self-securing. The electrode hub must move backward and outward to become dislodged. The closer A1 is to 90 degrees, the greater such resistance to dislodgement by lead manipulation. Taping over the hub 210 may provide additional stablilization of the electrode placement against disruption with inadvertent electrode lead manipulations.

In contrast to straight needle electrodes, which cross electrically inactive skin and subcutaneous tissue at a rather shallow angle after full insertion, the needle modification including, for example, proximal segment 220 traverses inactive skin and subcutaneous tissue at a steeper angle. This maximizes the depth of insertion that may be achieved relative to a straight needle of comparable length. Also, this minimizes a portion of the needle (proximal segment 220) that contacts inactive muscle tissue, and maximizes a portion of the needle electrode (terminal segment 230) that is situated within active muscle tissue. While polytetrafluoroethylene coating, such as TEFLON coating, of the proximal needle segment 220 may be additionally advantageous in order to limit the relative proportion of needle contact with inactive tissue, it may be less important with the modification.

Because of the two needle bends A1, A2, the modification may appear significantly shorter than a straight needle of the same length. The shorter appearance may aid in end user comfort. The flat-to-the-skin positioning of the hub 210 after placement may also be aesthetically pleasing and may also enhance end user acceptance.

The A2 angle may be chosen to best align the active portion of the electrodes, including proximal segment 220 and terminal segment 230, within the target muscle. Since facial muscles are oriented parallel to the skin, A2 should be roughly equal and opposite to Al, so that the active portion of the electrode may be parallel to the skin and the plane of the facial muscles. For deeper, non-planar or thicker target muscles, a more obtuse angle of A2 may be chosen, so that the active portion of the electrode may course more deeply into the target muscle.

Figure 3:
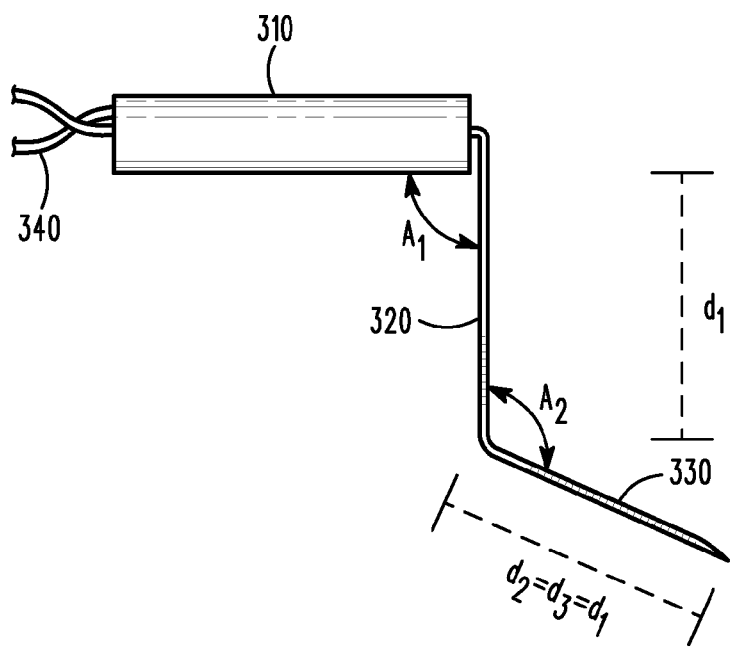
FIG. 3 is a "special" embodiment of needle modification of single or multi-needle electrodes with open angle at A2 in order to achieve increased depth of insertion in accordance with one possible embodiment of the disclosure.

FIG. 3 shows an embodiment with an open angle at A2, which enables a greater depth of insertion. In particular, FIG. 3 shows an embodiment 300 including a hub 310. A proximal needle segment 320 extends from the hub 310 at a first bend to define an angle A1 therebetween of 90 degrees. The proximal needle segment 320 extends to a second bend. A terminal needle segment 330 extends from the second bend to an end of the needle, wherein the terminal segment defines with the proximal segment 320 an angle A2 of greater than 90 degrees. Cables 340 extend from the hub 310 for connection to a monitoring device (not shown). Straight needle electrodes are typically inserted at a shallow angle with the skin. During needle insertion, the skin facilitates initial skin penetration by providing resistance along its surface. The above modified needle embodiments 100, 200 and 300 may be inserted at a steeper angle, relative to the skin surface. To achieve a proper overall insertion of a needle, the terminal segment must be inserted at an initial insertion angle that approximately corresponds to an angle between a proximal segment and a hub from which the needle extends. Therefore, an insertion angle of the terminal segment of embodiments 100, 200, and 300 should be 90 degrees relative to the skin. With a 90 degree insertion angle, however, there is no force vector along the skin surface, and resistance tension along the skin surface cannot aid in initial skin penetration. As such, in alternative embodiment, an angle A1 that is greater than 90 degrees may be implemented, so that at least some insertion force will be applied parallel to the skin surface wherein skin tension aids in skin penetration.

Figure 4:
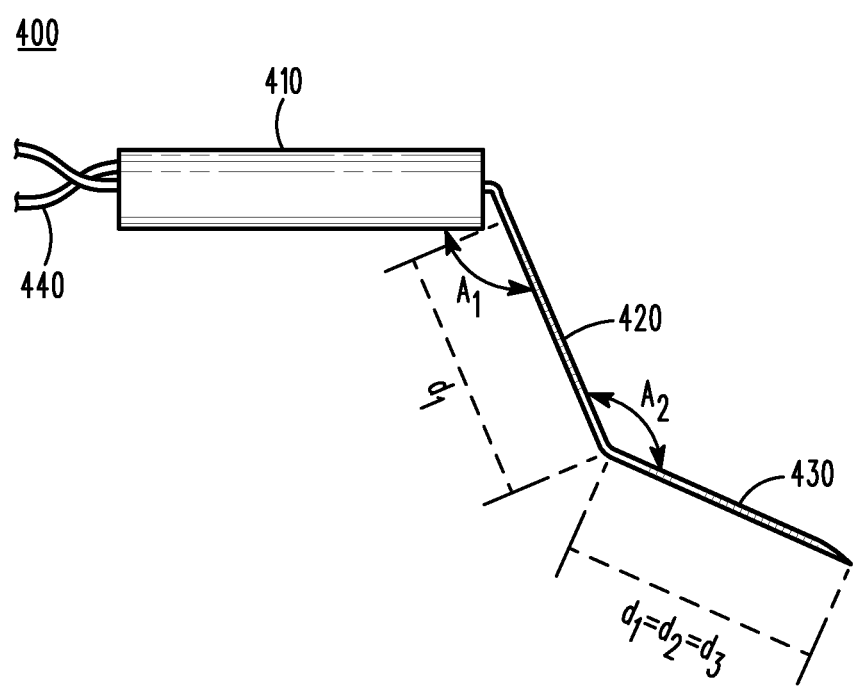
FIG. 4 is a "special" embodiment of single or multi-needle electrodes with open angles at A1 and A2 in accordance with one possible embodiment of the disclosure.

FIG. 4 shows an embodiment with A1 at 115 degrees and A2 at 125 degrees, for example. The terminal segment of this electrode 400 may be inserted at a 115 degrees angle (equal to A1) with skin in order that the hub 410 will end up flat on top of the skin surface. The slightly open angle of A1 may provide that there will be a force vector along the skin surface. The proximal needle segment 420 may traverse skin and subcutaneous tissue at a mildly open angle, versus a perpendicular orientation. Thus, it may achieve less depth after insertion than with A1 and A2 at 90 degrees, given a proximal needle segment of the same length. The larger angle at A2, relative to A1, may provide a (compensatory) deeper penetration of the terminal segment 430. Thus, within the "special" embodiment, A1 and A2 parameters may be coordinated in order to achieve the proper angle of insertion, as well as, the depth and orientation of the terminal needle segment 430.

2. Hub Modification of EMG Needle Electrodes with "Offset" Configuration

Subdermal (single needle) and multi-needle EMG electrodes are widely used during various intraoperative biophysiological monitoring procedures. A proposed modification of straight needle electrodes, incorporates two bends (angles A1 and A2) of the needle portion of EMG electrodes (FIG. 1). The modification is intended to increase stability and reliability of placement. A "special" embodiment of the general design incorporates equal lengths of the proximal and distal needle segments d1 and d3 and the initial insertion depth d2. With such embodiments, the entire terminal segment is inserted into the skin, so that the second angle A2 serves as a depth guide (FIGS. 2-4).

The terminal segment of the needle electrode is inserted at an angle with the skin surface, equal to the first angle A1. For "special" embodiments, the terminal needle segment(s) is/are completely inserted to the level of A2. The hub is then rotated backward so that its undersurface of the hub is parallel to the skin surface. Final positioning of the electrode is achieved by advancing the hub forward, while maintaining the "parallel with the skin" orientation of the hub. This is best achieved with the index finger and thumb on opposite sides of the hub. Pressure is applied to the sides of the hub so as to tip the electrode slightly upward as the hub is advanced forward. During forward advancement of the hub, the applied forward force should be exclusively parallel with the skin surface. When the hub has been advanced adequately, the electrode will drop into place, as the proximal needle portion enters the initial needle tract. When properly inserted, the electrode hub lies flat, immediately on top of the skin surface. This final physical relationship, between the electrode hub and the skin surface, provides quality assurance feedback to the end user regarding the fidelity of electrode placement.

The placement procedure for single and multi-needle electrodes with such an offset configuration involves different manual manipulations than for straight needle electrodes.

Straight needle electrodes are typically placed with the index finger and the thumb positioned below and on top of the hub, respectively, or with the thumb and index finger on either side. Insertion is a simple forward advancement along the needle alignment.

By contrast, the proposed modified needle electrodes are placed with an initial orientation of the needle terminus at an angle to the skin surface, which is equal to A1. The index finger may initially be on top of the hub and the thumb on the bottom. The next step in the placement procedure is to rotate the electrode hub downward until the hub is roughly parallel to the skin surface. The final step is the forward advancement of the electrode hub, while tipping the needle end slightly upward, so that the hub maintains is orientation parallel to the skin surface.

Present, low-profile, rounded-rectangular electrode hubs are rather difficult to manipulate, when they are close to the skin surface. It is a premise of the disclosed embodiments that the hub shape may be modified in order to aid in the ability to manipulate electrodes with an offset-needle modification during the placement procedure.

Figure 5A:
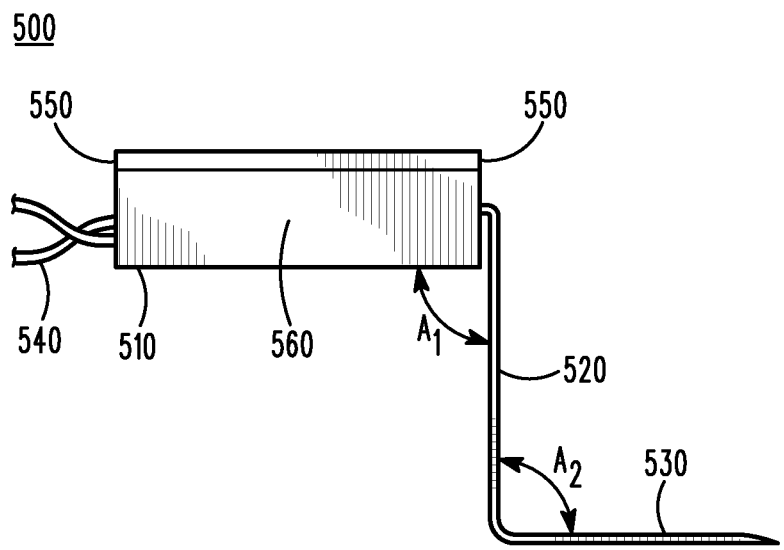
FIG. 5A is a side view of modified electrode hub for use with "offset" needle modifications in accordance with one possible embodiment of the disclosure.
Figure 5B:
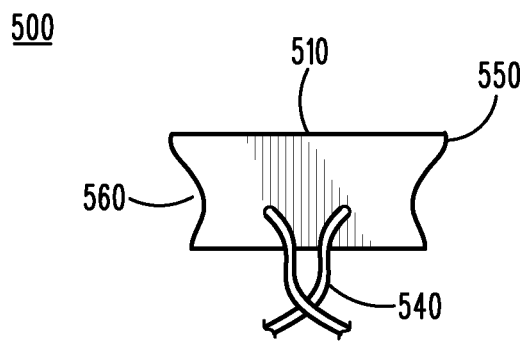
FIG. 5B is a rear view of modified electrode hub for use with "offset" needle modifications in accordance with one possible embodiment of the disclosure.

The disclosed embodiments may concern a modification for single and multi-needle EMG electrodes with an offset configuration 500. The modification may include a concave groove 560 and a relatively prominent upper ridge 550 along the sides of the hub 510, as shown in FIGS. 5A and 5B. The ridge 550 and groove 560 along the upper side-edges of the hub 510 may improve the ability to manually manipulate the hub 510 when it is parallel with, and close to, the skin. The ridge 550 and groove 560 may also be particularly helpful in maintaining a slight elevation of the electrode tip, in order to maintain the hub 510 in a plane parallel to the skin surface, as the electrode is advanced forward to its final position. With the ridge 550 along the upper edge of the sides of the electrode hub 510 may serve as a possible alternative to increasing the hub thickness in order to achieve better tactile feedback and manipulative control during placement.

Further refinements of the basic features might include multiple small vertical grooves along the lateral edges of the ridges 550 and/or in the grooves 560, in order to enhance the positive tactile feel of the sides of the hub 510.

3. Modified Ground Electrode for Intraoperative Nerve Integrity Monitoring

EMG recording during intraoperative nerve integrity monitoring may be performed using differential bipolar amplification, which incorporates a ground electrode in addition to a differential pair of active recording electrodes. The ground electrode is usually placed in or around the field of recording, separately from placement of the recording electrodes. The ground electrode is separate from the recording electrodes and is not presently used in any fashion to help facilitate the electrode setup.

The most common application of nerve integrity monitoring is facial nerve monitoring. Currently available facial nerve monitoring electrodes are in packages containing multiple electrodes. Individual electrodes are individually coiled up and lie free within the package. The end user must uncoil each electrode and place them separately. It is up to the end user to organize the electrodes in a manner that will minimize the possibility of electrode dislodgement and interference by mechanical or electrical artifacts.

In the case of facial nerve monitoring, the ground electrode has been variously placed in the hairline, the upper chest area or contralateral shoulder, with no consensus with regard to a preferred or "standard" location of the patient-ground electrode placement. Because the electrodes are packaged individually, with no design elements to imply a preferred setup arrangement of electrodes, there may be significant variability in setup among end users. The relative lack of standardization may result in untoward inconsistency in recording quality.

This disclosed embodiment may concern that the design and positioning of the ground electrode may be tailored to facilitate, organize and standardize the setup procedure.

In particular this disclosed embodiment may concern a modification of the ground electrode, where the electrode hub is physically, but not necessarily electrically, attached to the lead wires of the recording electrode(s). The attachment may be fixed, detachable or adjustable in position along the length of the lead wires, depending upon the requirements of individual applications. With such an attachment, the recording electrode lead wires may be supported and organized around a strategic placement position for the ground electrode.

During ear, parotid and skull base procedures, for which facial nerve monitoring is commonly employed, the head is typically turned away from the side to be operated. In this position, the contralateral shoulder is in reasonably close physical proximity to the ipsilateral (surgical) side of the face. This location is also in the general path of the electrode leads, as they course toward the point of connection with recording equipment at the "head box." In the interest of setup standardization, the contralateral shoulder may be elected as a possible site for the ground electrode placement. The ground electrode hub may be modified to attach the recording electrode leads at that site. This will support and organize the electrode leads during the setup and "standardize" the ground location. In the package, the electrodes may be arranged in a single coil, in a more easily-managed fashion, so that uncoiling the electrodes and their placement may be facilitated.

Figure 6A:
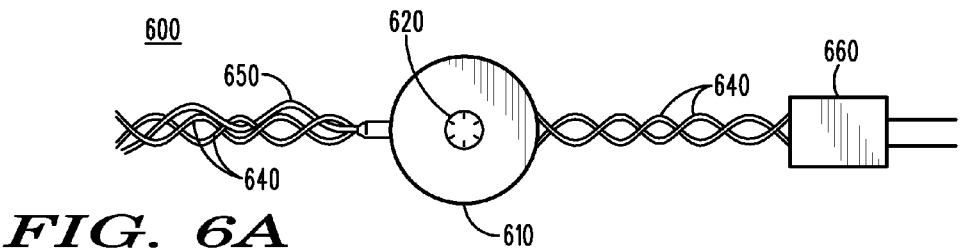
FIG. 6A is a bottom view of modified ground electrode that employs a standard electrocardiogram (ECG) snap lead in accordance with one possible embodiment of the disclosure.
Figure 6B:
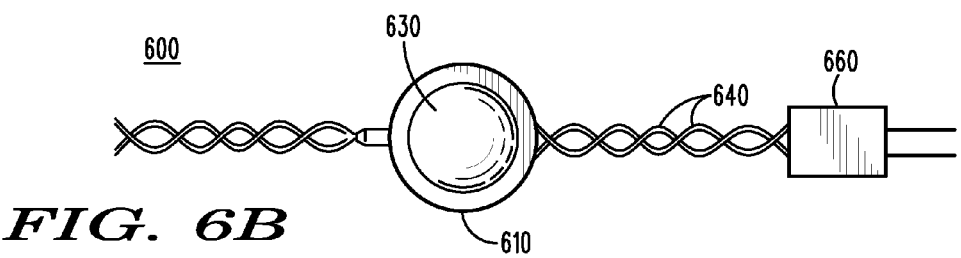
FIG. 6B is a top view of modified ground electrode that employs a standard ECG snap lead in accordance with one possible embodiment of the disclosure.
Figure 6C:
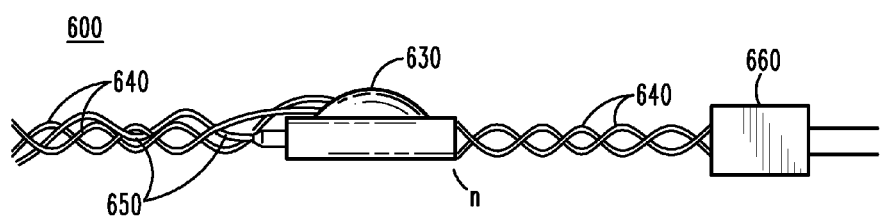
FIG. 6C is a side view of modified ground electrode that employs a standard ECG snap lead in accordance with one possible embodiment of the disclosure.

The ground electrode itself may include a needle electrode with a curved, straight, angled, or "offset" configuration. The needle hub may be modified to allow a fixed, detachable or adjustable (sliding) attachment to single or multiple recording electrode leads. The rather generous skin surface available at the contralateral shoulder site for facial nerve monitoring may also be amenable to the use of a "snap lead" style of surface electrode to which the recording electrode leads may be attached. FIGS. 6A-6C show an exemplary snap electrode lead 640 with a typical round disk hub 610 and a female snap 620 on the undersurface.

On the side opposite of the snap 620, a single or set of multiple recording electrode lead(s) 640 are attached to the hub 610. The attachment is at 630. In this embodiment, the electrode leads 640 are fixed to the hub 610. However, the leads 640 may be otherwise attached by a plastic or metal loop extending from the snap-lead hub 610 that may allow the electrode leads 640 to slide through, but not escape the hub attachment 630. Additional embodiments may involve detachable connections of the electrode leads 640 to the ground electrode hub 610, such as with Velcro dots or magnetic chips, for example.

The distance "d" from the recording electrode hub(s) 610 and the attachment point 630 to the ground electrode 650 may be elected to best support the electrode leads 640 in a possible location and orientation, proximate to the field of recording and where manipulations of surgical drapes are less/least likely to provoke mechanical artifacts. For facial nerve monitoring the distance may be approximately 12-15 inches for placement of the ground at the contralateral shoulder. In other applications, the positioning of the attachment of the patient-ground to the recording electrode lead wires may vary widely, depending upon the needs of individual setups. In some cases, the distance "d" may be much shorter in order to best organize the electrode leads 640 "out of the way" of the surgical procedure or in a manner so as to reduce potential electrical or mechanical artifacts. This configuration may be especially helpful for applications during which the recording electrodes 660 may be placed "on the field" in sterile fashion in or around the surgical field.

From the patient-ground electrode hub 610, the recording electrode leads 640 and the ground electrode lead 650 may run to their termination at the recording equipment "head box". The leads may 640, 650 may be organized or held together by braiding the ground lead 650 with a single electrode pair 640 or by taping or shrink wrapping multiple leads at selected intervals, for example. Such organization may facilitate the setup in that there is only one coil of electrode wires to unwind out of the package. Color coding or employ of a single proprietary terminal connector may facilitate proper connections to the recording equipment.

4. Multi-Application (Hybrid) Recording Electrode for Intraoperative Nerve Integrity (EMG) Monitoring.

Standard single or paired needle recording electrodes are simple and robust for use in most common applications in nerve integrity monitoring. However, their rigid construction may cause instability of placement and possible injury when needle electrodes are used to record EMG activity from delicate musculature or when there may be significant movement around the recording site area.

Hooked-wire electrodes have been used to record from delicate muscles in the pharynx and larynx. They have also been used to record from extremity musculature during active exercise, due to their stability of placement and minimal tendency for migration.

Figure 7A:
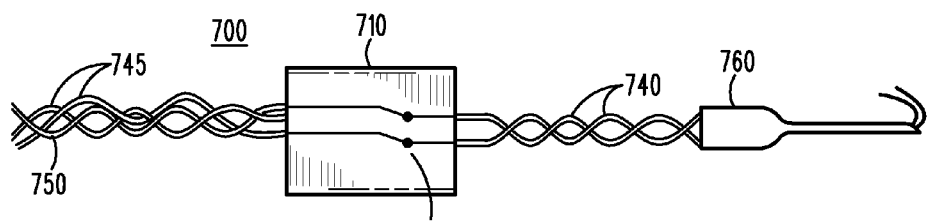
FIG. 7A is a top view of hybrid recording electrodes with hook wire electrodes electrically connected to standard electrode leads within the hub of a modified ground electrode in accordance with one possible embodiment of the disclosure.

This disclosed embodiment may concern a modification of a modified ground electrode 750, where the electrode leads may attach to the hub 710 of the ground electrode 750. In this case, however, there may be hard electrical connections 720 within the hub 710 of the ground electrode, connecting the terminal 745 and proximal 740 portions of the recording electrode leads, as shown in FIG. 7A. This disclosed embodiment may combine the delicate and stable attributes of hooked-wire electrodes 760 and the robustness of standard electrode leads. The inserted portion of the electrode 760 may be a bipolar fine hooked-wire electrode 760, the lead length of which d1 may be limited to only that required for unencumbered insertion into the target muscle tissue and subsequent placement of the hub 710 at a possible location.

Figure 7B:
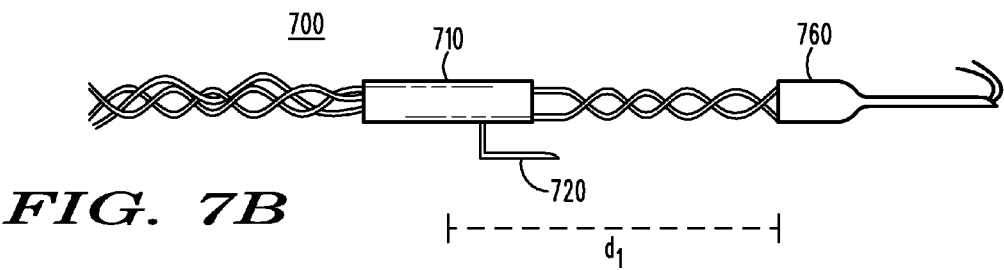
FIG. 7B is a side view of hybrid recording electrodes, with hook wire electrodes electrically connected to standard electrode leads within the hub of a modified ground electrode in accordance with one possible embodiment of the disclosure.

FIGS. 7A and 7B show an iteration of hooked-wire electrode 760 with the leads threaded through the entire length of the insertion hypodermic needle. This configuration may be for illustrative purposes to show the staggered arrangement of the bare portions of the wire electrodes. A possible embodiment may include having the terminal ends of the wires being backed into the terminal end of the hypodermic needle (Parker). This may allow for the needle to be completely removed after insertion.

The connection to existing nerve integrity monitoring equipment may be made by a supplemental length L2 of standard electrode leads 745 with standard or proprietary terminal connectors. The two wire types may be electrically connected 720 at the hub 710. After placement, the hub 710 may be taped or sewn into place near the recording site in order to secure the electrode placement. Paired notches or grooves or small tabs with holes may be incorporated in order to aid in securing the hub with a single suture.

A possible hub embodiment may be that of a modified ground electrode incorporating a modified ("off-set") needle electrode, as discussed below for example. Incorporation of a ground electrode at the hub may aid in supporting the delicate hooked wire electrodes and may standardize the relative positioning of the recording and ground electrodes.

5. Strategic Needle Positioning On Electrode Hub as an Aid and Quality Assurance Guide to Proper Depth of Placement Subdermal (single) and multi-needle EMG electrodes are widely used during various intraoperative biophysiological monitoring procedures. Previous modifications of these electrodes involve an "offset" configuration of the needle portion, which is intended to increase stability and reliability of placement (FIGS. 1-4). Insertion of so-modified electrodes is performed by initially entering the skin with the distal (sharp) portion of the needle at an angle to the skin surface, equal between the undersurface of the hub and the proximal needle segment A1. The needle is inserted to the desired (final) depth, after which the electrode is rotated backward so that the hub is roughly parallel to the skin surface. Electrode insertion is continued by forward advancement of the hub, parallel with the skin surface, while tipping the electrode slightly upward. Insertion is completed as the proximal segment of the needle drops into the track made during initial insertion.

When properly placed, the electrode hub lies flat, immediately on the skin surface. This final physical relationship, between the electrode hub and the skin surface, provides quality assurance feedback to the end user regarding the fidelity of electrode placement.

In conventional needle electrode designs, the needles originate from the anterior face of the hub. In order that the underside of the hub is positioned flat and on top of the skin surface, the depth of initial insertion must be of equal length to the proximal needle segment. For "special" embodiments of the "offset" needle modification, where proximal and distal needle segments are of equal length (FIGS. 2-4), the second needle bend at A2 serves as a depth guide. However, if the terminal needle segment is longer than the proximal segment (as in FIG. 1), the end user must match the initial insertion depth to the length of the proximal needle segment. If the initial insertion is too shallow, the hub will sit off of the skin surface. If the initial insertion is too deep, the hub will place pressure in the skin surface and will not sit flat on the skin surface.

The special embodiment cannot be used for shallow insertion depths, in that the overall needle length must be at least a centimeter in order to achieve the desired electrical impedance. Also, shorter needle lengths will not be as resistant to dislodgement with inadvertent lead manipulation.

This disclosed embodiment may concern a modification of needle electrodes with "offset" configuration, specifically with regard to the positioning of the electrode needles on the hub. The "offset" needle electrodes may be constructed so that the front edge of the hub can serve as a guide to the proper insertion depth for individual applications. Placement of the needle on the hub may vary for different depths of insertion, depending upon the specific application. For example, intramuscular placement may require a greater insertion depth than subdermal placement.

Figure 8A:
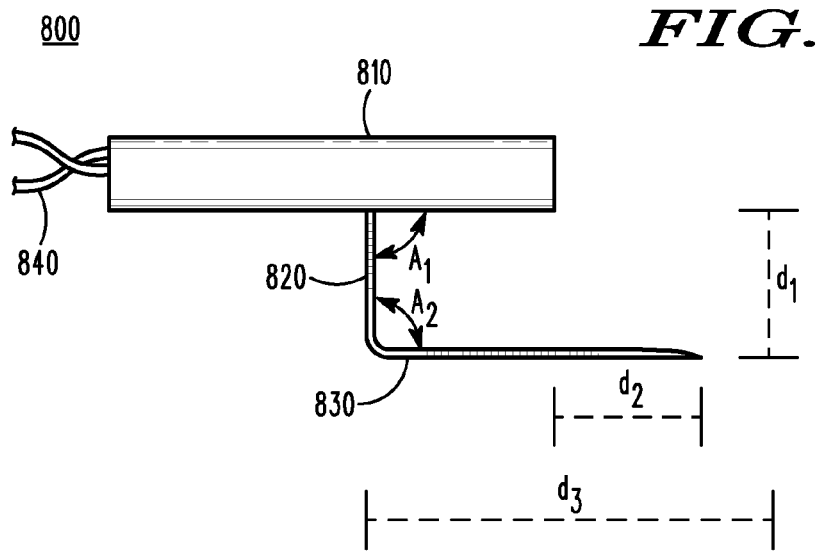
FIG. 8A is a side view of modification of the needle positioning on the electrode hub in order to provide a depth guide for electrode placement in accordance with one possible embodiment of the disclosure.
Figure 8B:
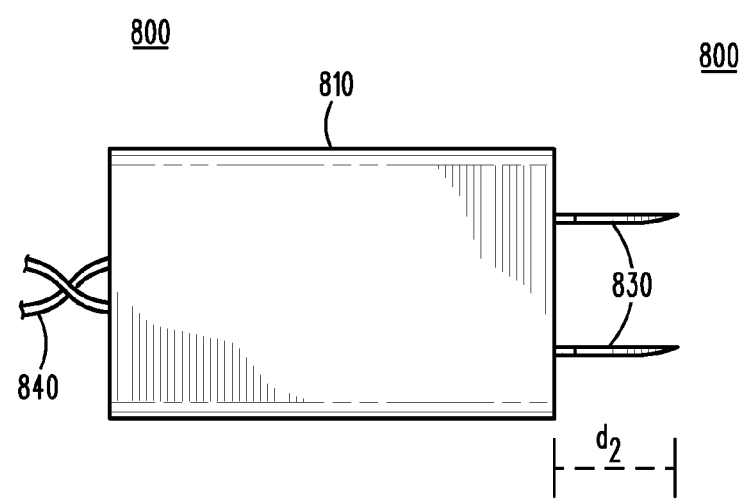
FIG. 8B is a top view of modification of the needle positioning on the electrode hub in order to provide a depth guide for electrode placement in accordance with one possible embodiment of the disclosure.

FIG. 8A shows the modification of the "offset" needle electrode 800. The needle 820, 830 may originate perpendicularly from the undersurface of the hub 810, which obviates the need for the first needle bend at A1. The length d1 of the proximal needle segment 820 may be elected to be the final depth.

In order that the underside of the electrode hub sits flat on top of the skin at the end of placement, the depth of initial needle insertion d2 may be equal to the length d1 of the proximal needle segment 820. This possible embodiment may position the origin of the needle along the hub 810, so that the needle terminus (sharp end) may extend a strategic distance, equal to d1 (and d2), from the front edge of the hub 810.

During the insertion procedure, the needle terminus 830 may be inserted, perpendicular to the skin surface, until the front edge of the hub 810 meets the skin surface. Thus, the front edge of the hub 810 may serve as a guide for initial insertion depth. The electrode placement is completed by rotating the hub 810 backward until it is oriented parallel with the skin surface. With the anterior aspect of the hub 810 tipped up slightly, so that the hub 810 is roughly parallel to the skin surface, the hub 810 may be advanced forward until the proximal needle segment enters the initial insertion path. The distance of forward advancement may be the length d3 of the terminal needle segment 830.

Figure 9A:
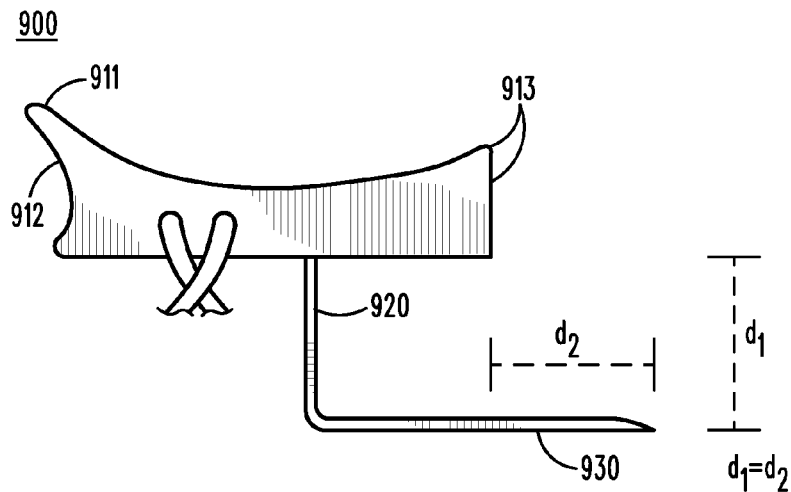
FIG. 9A is a side view of modified ground electrode incorporating modified needle positioning on the hub in accordance with one possible embodiment of the disclosure.
Figure 9B:
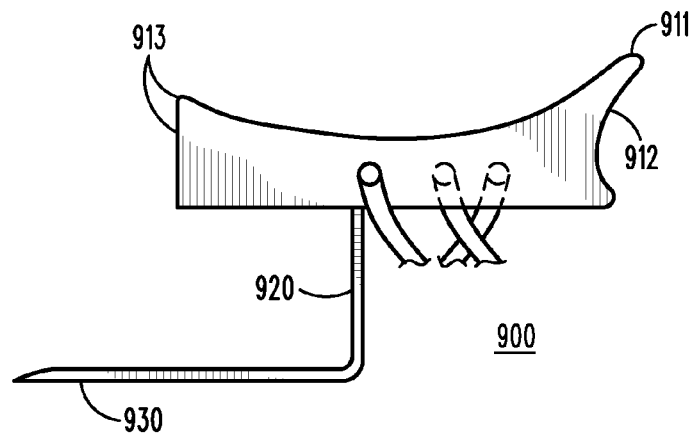
FIG. 9B is an opposite side view of modified ground electrode incorporating modified needle positioning on the hub in accordance with one possible embodiment of the disclosure.
Figure 9C:
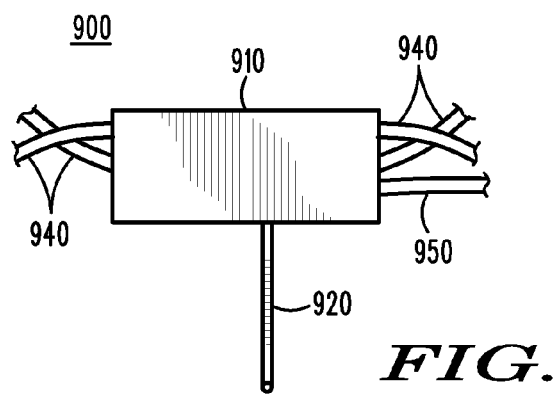
FIG. 9C is a front view of modified ground electrode incorporating modified needle positioning on hub in accordance with one possible embodiment of the disclosure.

FIGS. 9A-9C may combine an alternative embodiment 900 of a modified ground electrode and the modified placement of the needle on the hub. The length d1 of the proximal needle segment 920 may be equal to the length d2 of the portion of the terminal needle segment 930, beyond the anterior edge of the needle hub. The recording electrode leads 940 and the ground lead 950 may be oriented perpendicular to the needle, in order to allow the mechanical manipulations required for needle placement. The needle hub 910 may be modified from a typical rounded rectangular configuration. There may be a ridge 911 and groove 912 on the back aspect of the hub, as well as a ridge and flat anterior surface 913 on the front aspect of the hub. These hub 910 features may facilitate placement of the electrode, with the thumb on the back and index finger on the front of the hub. The electrode leads 940, 950 may interfere with placing the thumb and index finger along the sides of the hub.

The ridge 911 on the back of the hub 910 may extend backward at approximately a 45 degrees angle, which facilitates working the back of the hub up and down with the thumb. The front ridge 913 may be vertical and flat with the front face of the hub. The prominent front edge of the hub may aid in keeping the electrode tipped up slightly, with the index finger, during the final horizontal and forward movement of electrode insertion. The flat portion may also help the user establish insertion depth d2.

The modification may render the anterior edge of the needle hub 910 as a guide to proper depth of placement. It is expected to facilitate proper electrode placement by the end user and further reduce untoward variability of recording quality.

6. Three-Needle Electrode, Low-Noise EMG Recording Electrode for Intraoperative Nerve Integrity Monitoring and its Method of Connection with Recording Equipment Intraoperative nerve integrity monitoring provides auditory feedback, which increases the surgeon's awareness of the physical contour of the monitored nerve and the possible injurious effects of ongoing surgical manipulations. The procedure involves use of differential amplification of EMG signals, employing a pair of recording electrodes and a ground electrode. While the recording electrodes have been incorporated in a paired configuration with a single hub, the ground electrode is placed separately in relative proximity to the field of recording. The ground electrode, used in differential amplification, helps control electrical artifacts, such as DC offset and common electrical noise.

As the use of intraoperative nerve integrity monitoring expands into other applications, maintenance of high quality recording with a minimum of electrical artifacts remains an important concern. False-positive electrical and mechanical artifacts may confound recording electrodes appear the most symmetrically and identically with the ground electrode positioned between the two electrodes. The disclosed embodiments extend from that concept and should adapt well to any application.

In conventional systems, ground and recording electrodes are available in packages with two or more recording electrodes. The end user must choose appropriate placement sites for the individual electrodes. There is likely to be significant variability in the setup with regarding to the placement and organization of electrode leads.

This disclosed embodiment may include a product design that may strongly leverage toward standardization of recording setup and reduction of electrical artifacts during intraoperative nerve integrity monitoring in a variety of possible future applications. From the perspective of a differential amplifier, the recording electrodes within a differential pair may appear the most identical/symmetric, when the ground electrode is positioned between them. The disclosed embodiments may derive from this concept and may aid in setup standardization and in maintaining high recording quality.

Figure 10A:
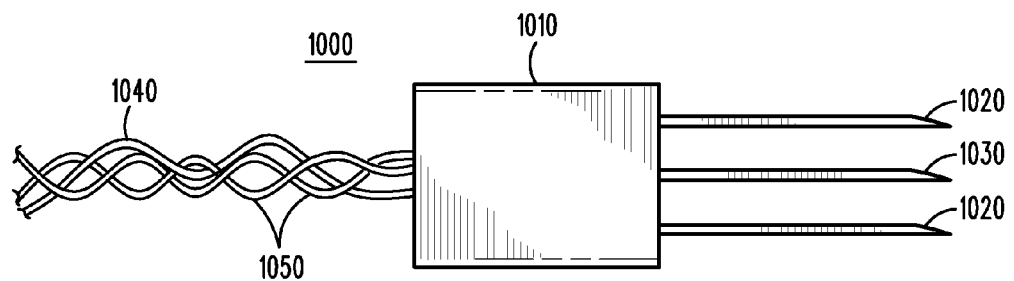
FIG. 10A is a top view of three-needle electrode incorporating a ground electrode between two active recording electrodes in accordance with one possible embodiment of the disclosure.
Figure 10B:
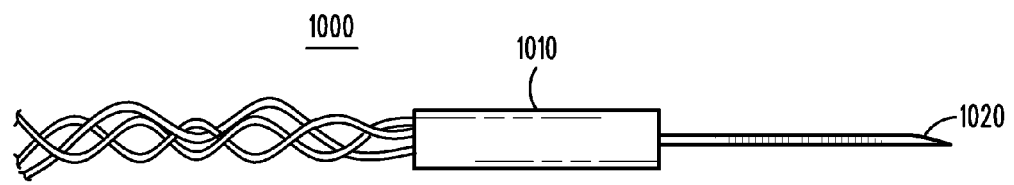
FIG. 10B is a side view of three-needle electrode incorporating a ground electrode between two active recording electrodes and a straight needle configuration in accordance with one possible embodiment of the disclosure.
Figure 10C:
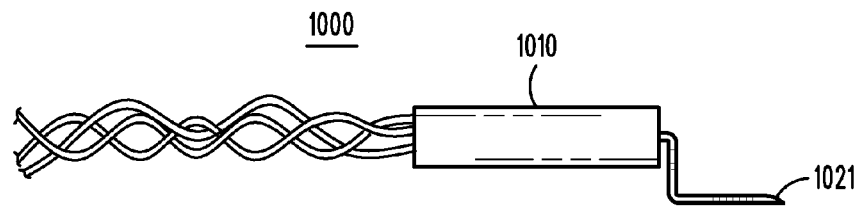
FIG. 10C is a side view of three-needle electrode incorporating a ground electrode between two active recording electrodes and modified ("offset") needle configuration in accordance with one possible embodiment of the disclosure.

In this manner, the disclosed embodiments may concern a modification of a paired electrode design where a third needle electrode 1030, as shown in FIGS 10A-10C, may be located symmetrically between the paired recording electrodes 1020, and may serve as the ground electrode in the electrode 1000 of FIGS. 10A-10C. The needle electrodes 1020, 1030, housing with a hub 1010, may be straight, as shown in FIG. 10B or modified with an offset configuration 1021, as shown in FIG. 10C. The electrode leads 1040, 1050 may be taped together at intervals, twisted together or braided in order to minimize the antenna-like qualities of the electrode leads themselves.

Conventional methodology may employ a single ground electrode with single or multiple recording electrodes. The disclosed embodiments may employ a ground electrode 1030 for each differential pair of recording electrodes 1020, for example. If multiple electrodes are used, there may be multiple ground electrodes, for example. All ground electrodes may be tied together electrically at one point, in order to avoid "ground loop" issues. Such a connection may be accomplished with external adaptor (Y-connector) devices, for example.

Figure 11:
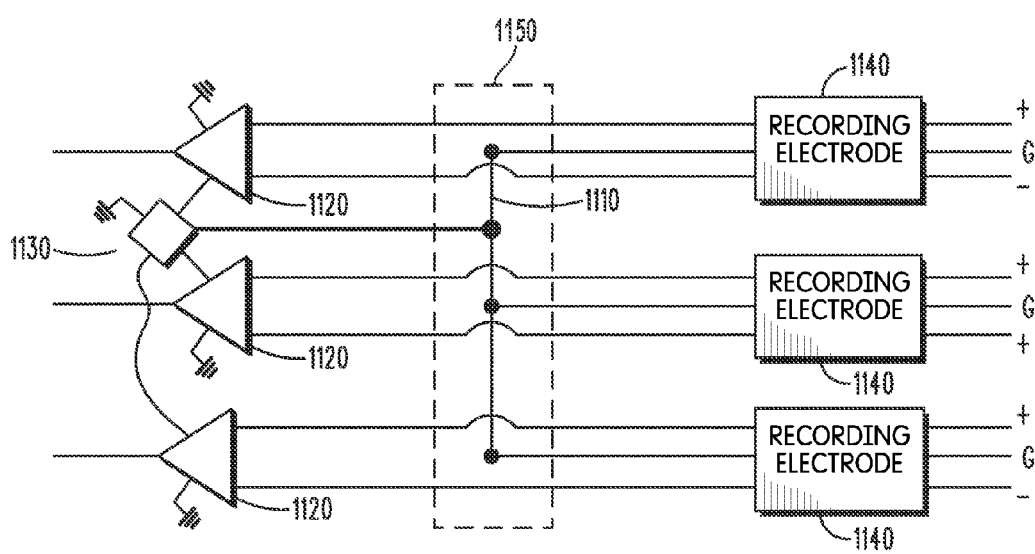
FIG. 11 is a single-point connection of ground electrodes when multiple three-needle electrodes are used in accordance with one possible embodiment of the disclosure.

Alternatively, internal modifications of the patient "head box" or within the main monitoring unit itself may provide an "internal" single-point connection. FIG. 11 shows a "single point" connection 1110 within the patient isolation "head box" 1150, which connects all needle ground electrodes 1130 of recording electrode 1140, and is located ahead of the input amplifiers 1120 within the main recording unit. The electrode leads may be terminated with proprietary three-lead terminal connectors to the headbox 1150 to further facilitate the setup by reducing the number of connections to be made. Additional circuitry may be implemented for adjusting the relationship between the chassis ground, patient ground, and the ground at individual input (initial gain stage) recording amplifiers 1120.

7. "Virtual" Anode Electrode for Intraoperative Nerve Integrity Monitoring

The disclosed embodiments may concern a modification of the method by which the anode ("return") electrode connection is achieved for the purposes of electrical stimulation during intraoperative nerve integrity monitoring.

Electrical stimulation is frequently performed during intraoperative nerve integrity monitoring in order to locate and map the physical contour of the monitored nerve. Stimulation is achieved by a flow of current through the nerve of sufficient intensity to produce nerve depolarization. Current flows from the cathode (negative) electrode to an anode (positive) electrode. The surgeon uses a handheld electrical stimulus probe, connected to the cathode, in order to deliver current the nerve contour. In monopolar applications, the anode may be placed at some distance, such as at the ipsilateral shoulder. For bipolar applications, the anode is positioned in close proximity to the cathode. Close pairing of the cathode and anode, confines current flow to a small area, enhancing spatial selectivity of electrical stimulation.

In possible applications, both the anode and cathode are active, electrically distinct from patient and chassis ground connections. If monopolar electrical stimulation is to be used, a separate anode electrode must be placed. If the need for electrical stimulation was not anticipated prior to the surgical procedure, but is found necessary sometime during the case, placement of the anode electrode "after the fact" under the surgical drapes may be difficult and disruptive to the flow of the surgical procedure.

The cathode electrode is has greater "stimulus adequacy" than the anode electrode, but current flow around an active anode electrode may also provoke nerve stimulation, when the anode is in physical proximity to the nerve. Stimulation around the anode may result in some ambiguity in locating the nerve contour, relative to the contact surfaces of the cathode and anode stimulus contacts.

Current flow around the anode can be eliminated by connecting the anode electrode to the ground, eliminating the possibility of nerve stimulation at the anode electrode. Use of the ground electrode as the stimulus anode connection obviates the need to place a separate anode electrode, which streamlines the setup.

Figure 12:
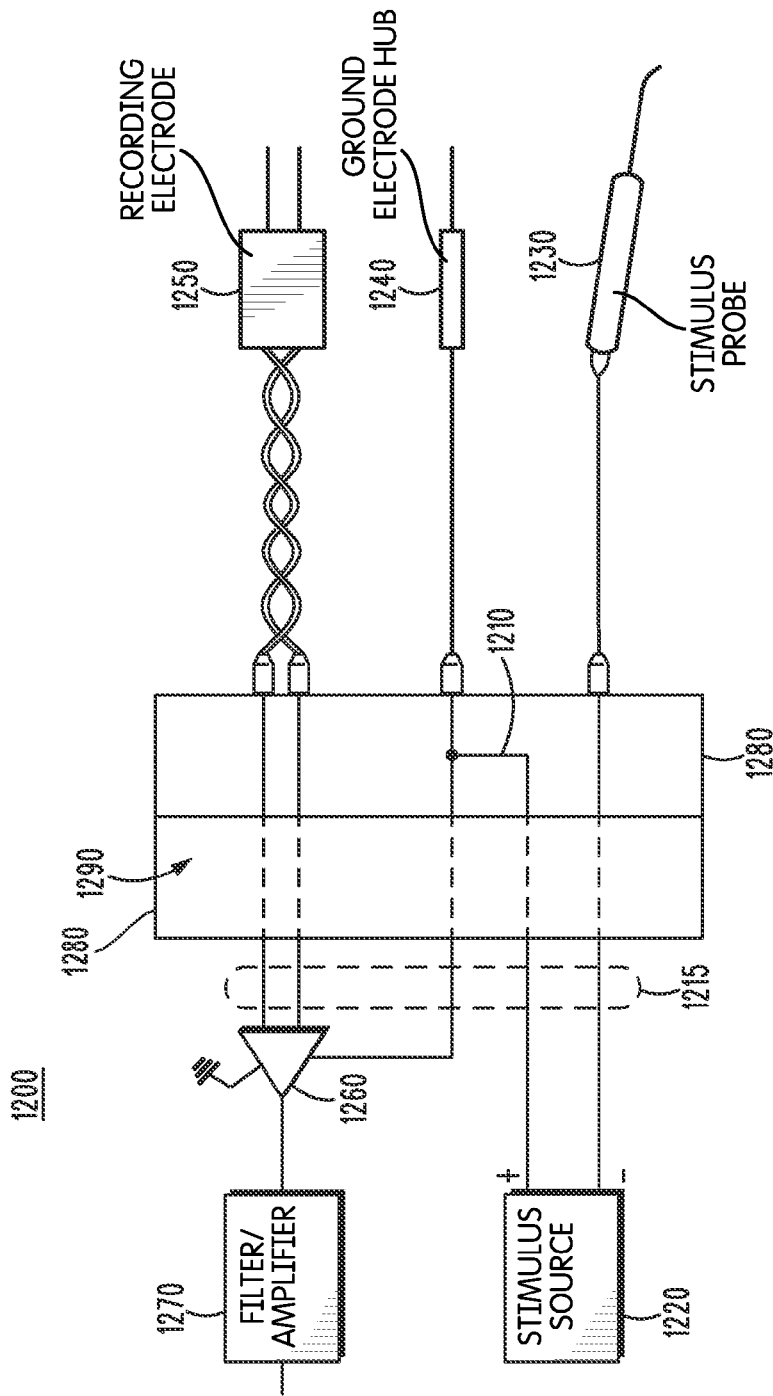
FIG. 12 is a "virtual anode" achieved by connecting the ground electrode to the anode connection before an electrical isolation circuit in accordance with one possible embodiment of the disclosure.

The disclosed embodiments may eliminate the need for a separate stimulus anode electrode during monopolar electrical stimulation and may reduce possible localization ambiguity during bipolar stimulation. FIG. 12 shows a virtual anode 1200 in accordance with an embodiment. The virtual anode includes a connection 1210 interposing a ground electrode circuit (within headbox 1280) to an anode of a stimulus source 1220. A handheld cathode stimulus probe 1230 is used to stimulate tissue in a probing fashion. A separate anode electrode connection to the patient (not shown) may be eliminated by connection of a ground electrode hub 1240 to the anode in the stimulus circuit. This may be accomplished before (e.g., on the patient side) or after (e.g., on the monitoring equipment side) the electrical isolation circuitry, but may not be across it. FIG. 12 also shows a recording electrode 1250. FIG. 12 shows an exemplary electrical connection 1210 between the ground electrode 1240 and the anode terminal. Connection 1210 is located before (e.g., on the patient side) the isolation circuit 1290. FIG. 12 shows additional filter and amplification components 1270 for minimizing stimulus and other artifacts, and amplifying signal to loudspeaker audio level. The headbox 1280 may contain both the isolation circuit 1290 and said connection 1210 as shown.

Figure 13:
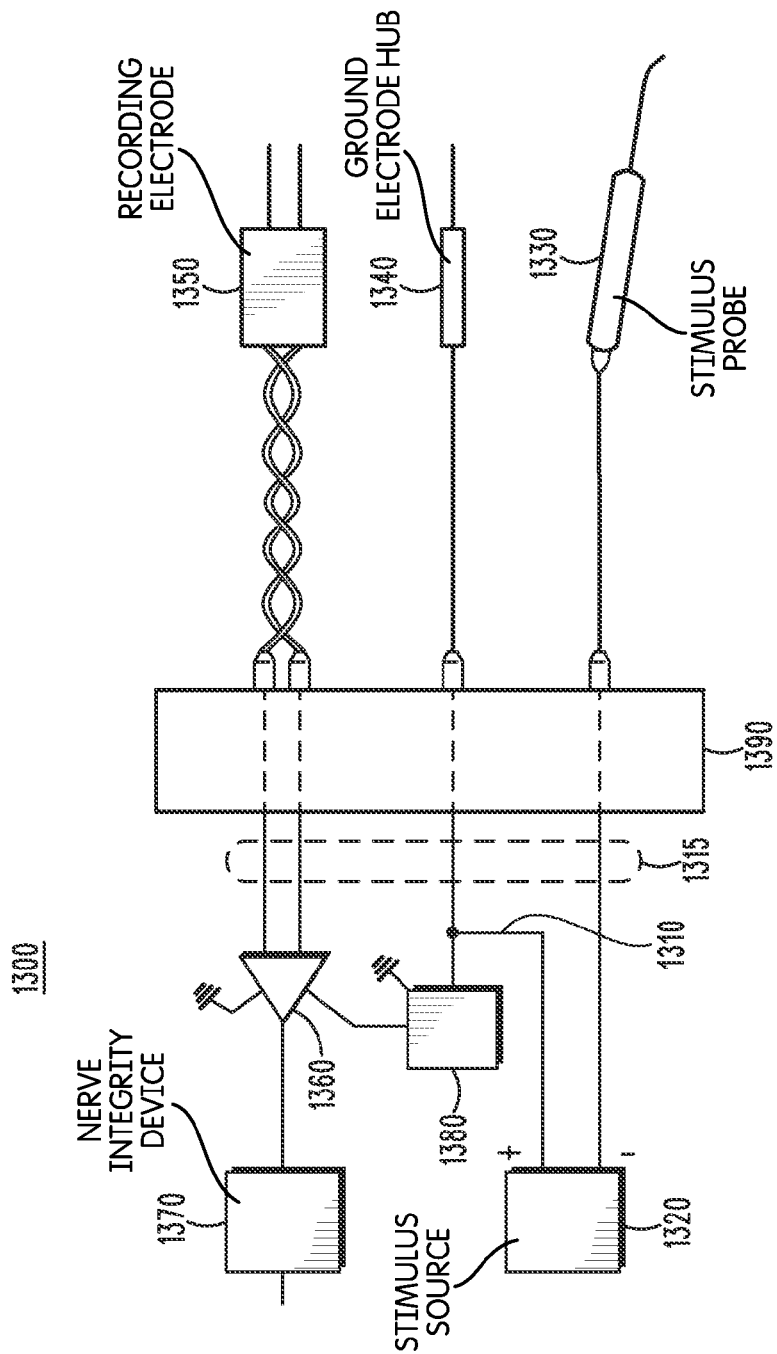
FIG. 13 is a "virtual anode" achieved by connecting the ground electrode to the anode connection, after an electrical isolation circuit in accordance with one possible embodiment of the disclosure.

A possible disadvantage of making the ground-anode connection before isolation may be that the harness 1215, containing multiple wires from the terminal electrode connections and the main monitoring unit, must include a connection 1210 such as a wire that ultimately connects to the anode terminal of the stimulus source 1220. FIG. 13 shows an alternative embodiment of a virtual anode 1300. The embodiment shown in FIG. 13 includes a connection 1310 between the ground electrode circuit and anode stimulus source 1320 "after (e.g., on the monitoring equipment side)" the electrical isolation circuit 1390, within the main unit. The possible interference from the stimulator circuit in the recording side of the monitoring function may be accomplished with a filter 1380, which separates the anode of the stimulus source 1320 from the ground of the differential amplifier 1360. Further, existing designated nerve integrity devices 1370 may mute the EMG recording signal during stimulus presentation, so that the end user cannot hear the stimulus itself FIG. 13 shows a handheld stimulus probe 1330 for locating nerve structure of a patient connected directly to the electrical isolation circuit 1390. FIG. 13 shows a ground electrode hub 1340, and a recording electrode 1350 connected directly to the electrical isolation circuit 1390.

An advantage of making the connection between the anode and ground electrode in this location may be that no wire for the anode connection 1310 is required in the patient connection harness 1315 between the main monitoring unit and the terminal electrode connections. A possible disadvantage might be the ability to prevent audible interference in the recording circuit and possibly more difficulty in satisfying FDA safety issues.

Either of the above embodiments may convert the electrical stimulation circuit from a "double-ended" to a "single-ended" configuration, through connection of the anode electrode to the ground electrode. This may result in neutralization of the anode electrode with regard to stimulus adequacy. This configuration may improve the spatial selectivity of bipolar stimulation. It may also obviate the need for separate placement of an anode electrode for monopolar stimulation. One may only need to connect the monopolar (cathode) stimulus probe to complete the circuit for monopolar stimulation, at any time during the surgical procedure.

Although the above description may contain specific details, they should not be construed as limiting the claims in any way. Other configurations of the described embodiments of the disclosed embodiments are part of the scope of this disclosure. For example, the principles of the disclosed embodiments may be applied to each individual user where each user may individually deploy such a system. This enables each user to utilize the benefits of the disclosed embodiments even if any one of the large number of possible applications do not need the functionality described herein. In other words, there may be multiple instances of the features in the disclosed embodiments each processing the content in various possible ways. It does not necessarily need to be one system used by all end users. Accordingly, the appended claims and their legal equivalents should only define the disclosed embodiments, rather than any specific examples given.

I claim:

1. An electromyographic (EMG) recording electrode assembly for intraopertaive nerve integrity monitoring, comprising:
   one or more cables enabled for connection directly or indirectly to a nerve integrity monitor;
   an electrode hub connected to the one or more cables; and
   one or more needle electrodes connected to the electrode hub, each of the one or more needle electrodes being an electrode configured to extend, along a line of insertion into a patient, from the electrode hub to a first bend, and to extend from the first bend in a first direction away from the electrode hub to a second bend, and to extend from the second bend in a second direction to an end of the electrode, defining a proximal needle segment from the hub to the second bend and a terminal needle segment from the second bend to the end of the electrode, wherein the terminal needle segment and at least a portion of the proximal needle segment are insertable into a patient along the line of insertion.

2. The electromyographic (EMG) recording electrode assembly of claim 1, wherein an angle between an undersurface of the electrode hub and the proximal needle segment is approximately 90 degrees.

3. The electromyographic (EMG) recording electrode assembly of claim 1, wherein an angle between the proximal needle segment and the terminal needle segment is approximately 90 degrees.

4. The electromyographic (EMG) recording electrode assembly of claim 1, the one or more needle electrodes being configured wherein a depth of an initial insertion by the one or more needle electrodes when inserted into a patient's skin is approximately equal to a length of the proximal needle segment.

5. The electromyographic (EMG) recording electrode assembly of claim 1, the one or more needle electrodes being configured wherein a depth of an initial insertion by the one or more needle electrodes when inserted into a patient's skin is approximately equal to a length of the proximal needle segment or a length of the terminal needle segment.

6. The electromyographic (EMG) recording electrode assembly of claim 1, the assembly being configured wherein an angle of an insertion by the one or more needle electrodes into a patient's skin is approximately equal to 90 degree with respect to the patient's skin.

7. The electromyographic (EMG) recording electrode assembly of claim 1, wherein the second bend is a depth guide for guiding a depth of initial insertion.

8. The electromyographic (EMG) recording electrode assembly of claim 1, wherein the one or more needle electrodes and the electrode hub being configured wherein when the one or more needle electrodes are inserted into a patient's skin, the electrode hub is enabled to lay flat on and parallel to the patient's skin surface.

9. The electromyographic (EMG) recording electrode assembly of claim 1, comprising at least a portion of the proximal segment having a coating comprising polytetrafluoroethylene.

10. The electromyographic (EMG) recording electrode assembly of claim 1, wherein an angle between the proximal needle segment and the terminal needle segment is greater than 90 degrees and less than 180 degrees.

11. The electromyographic (EMG) recording electrode assembly of claim 1, wherein an angle between the electrode hub and the proximal needle segment is greater than 90 degrees and less than 180 degrees.

12. The electromyographic (EMG) recording electrode assembly of claim 1, wherein the electrode hub has at least one concave groove and at least one upper ridge.

13. The electromyographic (EMG) recording electrode assembly of claim 1, wherein one of the one or more needle electrodes is a ground electrode.

14. The electromyographic (EMG) recording electrode assembly of claim 1, further comprising:
a cable hub, the cable hub being configured for attaching one or more electrode leads, the cable hub being configured to interpose the electrode hub and the nerve integrity monitor when the one or more cables are connected to the monitor.

15. The electromyographic (EMG) recording electrode assembly of claim 14, wherein the one or more cables are attachable and removable from the cable hub.

16. The electromyographic (EMG) recording electrode assembly of claim 14, wherein the cable hub is rounded.

17. The electromyographic (EMG) recording electrode assembly of claim 14, wherein the cable hub is connected to one or more cables that are attachable to and removable from the patient.

18. The electromyographic (EMG) recording electrode assembly of claim 14, wherein the cable hub serves as an active ground electrode.

19. The electromyographic (EMG) recording electrode assembly of claim 1, wherein the terminal needle segment is longer than the proximal needle segment.

20. The electromyographic (EMG) recording electrode assembly of claim 1, wherein the one or more cables are oriented perpendicular to the one or more needle electrodes.

21. The electromyographic (EMG) recording electrode assembly of claim 1, wherein the electrode hub has an indented portion where a user's thumb may be positioned to facilitate insertion of the electrode into a patient's skin.

22. The electromyographic (EMG) recording electrode assembly of claim 1, comprising:
a plurality of ground electrodes, the plurality of ground electrodes being consolidated in a single-point connection to the electrode hub.

23. The electromyographic (EMG) recording electrode assembly of claim 1, the one or more needle electrodes further comprising:
a stimulator anode electrode;
a ground electrode; and
a connection between the stimulator anode electrode and the ground electrode.

24. The electromyographic (EMG) recording electrode assembly of claim 1, wherein the one or more cables are attachable and removable from the electrode hub.

* * * * *